United States Patent
Shida

(10) Patent No.: US 8,440,984 B2
(45) Date of Patent: May 14, 2013

(54) FLUOROSCOPY SYSTEM

(75) Inventor: Hiromi Shida, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/597,978

(22) Filed: Aug. 29, 2012

(65) Prior Publication Data

US 2012/0319006 A1    Dec. 20, 2012

Related U.S. Application Data

(63) Continuation of application No. PCT/JP2011/053208, filed on Feb. 16, 2011.

(30) Foreign Application Priority Data

Mar. 3, 2010   (JP) .................................. 2010-046566

(51) Int. Cl.
   *F21V 9/16*   (2006.01)
(52) U.S. Cl.
   USPC ..................................... 250/458.1; 250/459.1
(58) Field of Classification Search ............... 250/458.1, 250/459.1
   See application file for complete search history.

(56) References Cited

U.S. PATENT DOCUMENTS

| | | | |
|---|---|---|---|
| 2002/0062061 A1* | 5/2002 | Kaneko et al. | 600/118 |
| 2005/0203423 A1* | 9/2005 | Zeng et al. | 600/476 |
| 2008/0161699 A1* | 7/2008 | Zeng et al. | 600/478 |
| 2009/0179159 A1* | 7/2009 | Yamada | 250/459.1 |
| 2011/0213252 A1* | 9/2011 | Fulghum | 600/476 |

FOREIGN PATENT DOCUMENTS

| | | |
|---|---|---|
| JP | 2005-081079 | 3/2005 |
| JP | 2005-204958 | 8/2005 |
| JP | 2005-319116 | 11/2005 |
| JP | 3771985 | 2/2006 |
| JP | 2006-189258 | 7/2006 |

OTHER PUBLICATIONS

English Abstract of corresponding Japanese Patent Publication No. JP 10-201700, dated Aug. 4, 1998.
International Search Report dated May 10, 2011 issued in PCT/JP2011/053208.

* cited by examiner

*Primary Examiner* — Christine Sung
(74) *Attorney, Agent, or Firm* — Scully, Scott, Murphy & Presser, P.C.

(57) ABSTRACT

Provided is a fluoroscopy system includes a light source device that emits white light and excitation light for irradiation of a subject; a white-light-image generating section that generates a white-light image by capturing the white light reflected from the subject; a fluorescence-image generating section that generates a fluorescence image by capturing fluorescence from the subject irradiated with the excitation light; an intensity-distribution generating section that generates a fluorescence intensity distribution of pixels of the fluorescence image; a peak-detecting section that detects a fluorescence-intensity peak in the fluorescence intensity distribution; a peak-count comparing section that calculates a count of the peak; an image-combining section that generates a combined image by superimposing a display representing a region including a pixel having the fluorescence intensity at the peak on the white-light image or the fluorescence image based on the peak count; and a monitor that displays the combined image.

8 Claims, 16 Drawing Sheets

WHITE-LIGHT IMAGE (NORMAL)

BUTTON DISPLAYED FOR SWITCHING BETWEEN
WHITE-LIGHT IMAGE AND FLUORESCENCE IMAGE

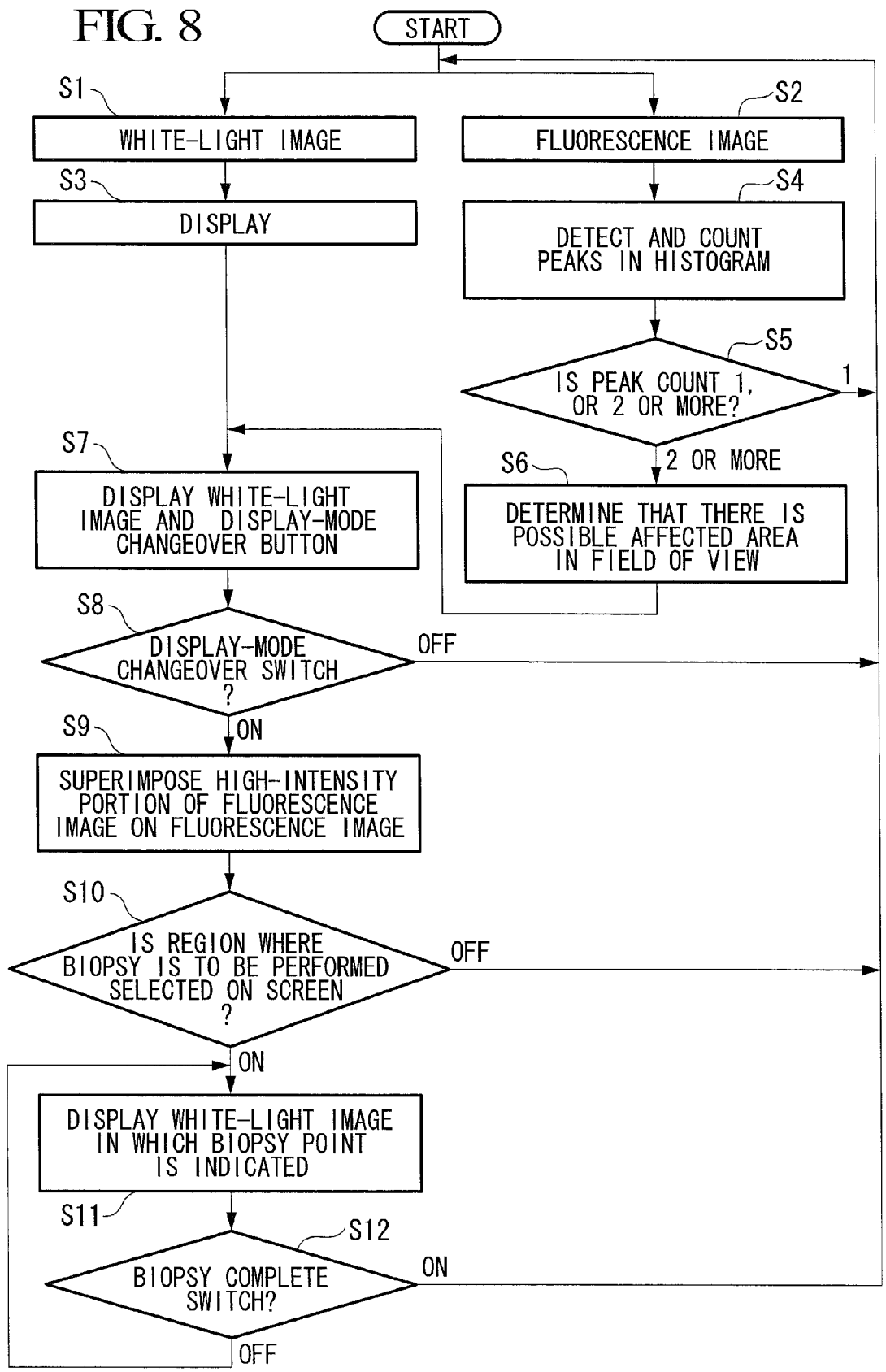

DISPLAY ASSIGNED COLORS

US 8,440,984 B2

FLUOROSCOPY SYSTEM

TECHNICAL FIELD

The present invention relates to fluoroscopy systems.

BACKGROUND ART

There are known fluoroscopy systems in the related art that locate an affected area by means of fluoroscopy, that allow the user to mark a point that needs biopsy (diagnosis using biological tissue), and that display the position corresponding to the marked point in a white-light image (see, for example, PTL 1)

CITATION LIST

Patent Literature

{PTL 1}
Publication of Japanese Patent No. 3771985

SUMMARY OF INVENTION

Solution to Problem

The present invention employs a fluoroscopy system including an illumination light source that emits white light and excitation light for irradiation of a subject; a white-light-image generating section that generates a white-light image by capturing the reflected light reflected on the subject irradiated with the white light emitted from the illumination light source; a fluorescence-image generating section that generates a fluorescence image by capturing fluorescence emitted from the subject irradiated with the excitation light emitted from the illumination light source; an intensity-distribution generating section that generates a fluorescence intensity distribution of pixels of the fluorescence image generated by the fluorescence-image generating section; a peak-detecting section that detects a fluorescence-intensity peak in the fluorescence intensity distribution generated by the intensity-distribution generating section; a peak-count calculating section that calculates a count of the peak detected by the peak-detecting section; an image-combining section that generates a combined image by superimposing a display representing a region including a pixel having the fluorescence intensity at the peak detected by the peak-detecting section on the white-light image or the fluorescence image based on the peak count calculated by the peak-count calculating section; and an image-displaying section that displays the combined image generated by the image-combining section.

The fluoroscopy system according to the above invention may further include a position-designating section via which a desired position is designated in the combined image displayed by the image-displaying section, and the image-combining section may generate the combined image by superimposing a display locating the position designated via the position-designating section on the white-light image.

In the fluoroscopy system according to the above invention, the image-combining section may generate the combined image by superimposing a display locating the pixel having the fluorescence intensity at the peak on the white-light image.

In the fluoroscopy system according to the above invention, if the peak-detecting section detects a plurality of peaks, the image-combining section may generate the combined image by superimposing a display representing the region on the fluorescence image.

In the fluoroscopy system according to the above invention, the image-combining section may generate the combined image representing a plurality of the regions corresponding to a plurality of peaks at different fluorescence intensities in different manners for each region.

In the fluoroscopy system according to the above invention, the image-combining section may represent the plurality of regions corresponding to the plurality of peaks at different fluorescence intensities in different colors.

In the above invention, the image-combining section may represent the region by using a boundary line surrounding the region.

The above invention may further include an area-designating section via which a desired area is designated in the combined image displayed by the image-displaying section, and the image-combining section may generate the combined image by further combining an enlarged image of an area of the white-light image corresponding to the area designated via the area-designating section.

BRIEF DESCRIPTION OF DRAWINGS

FIG. 8 is a flowchart showing a process executed by the fluorescence endoscope in FIG. 2.

DESCRIPTION OF EMBODIMENTS

First Embodiment

A fluoroscopy system 1 according to a first embodiment of the present invention will hereinafter be described with reference to the drawings. An application of the fluoroscopy system 1 according to this embodiment to an endoscope system 100 is described herein.

Figure 1:
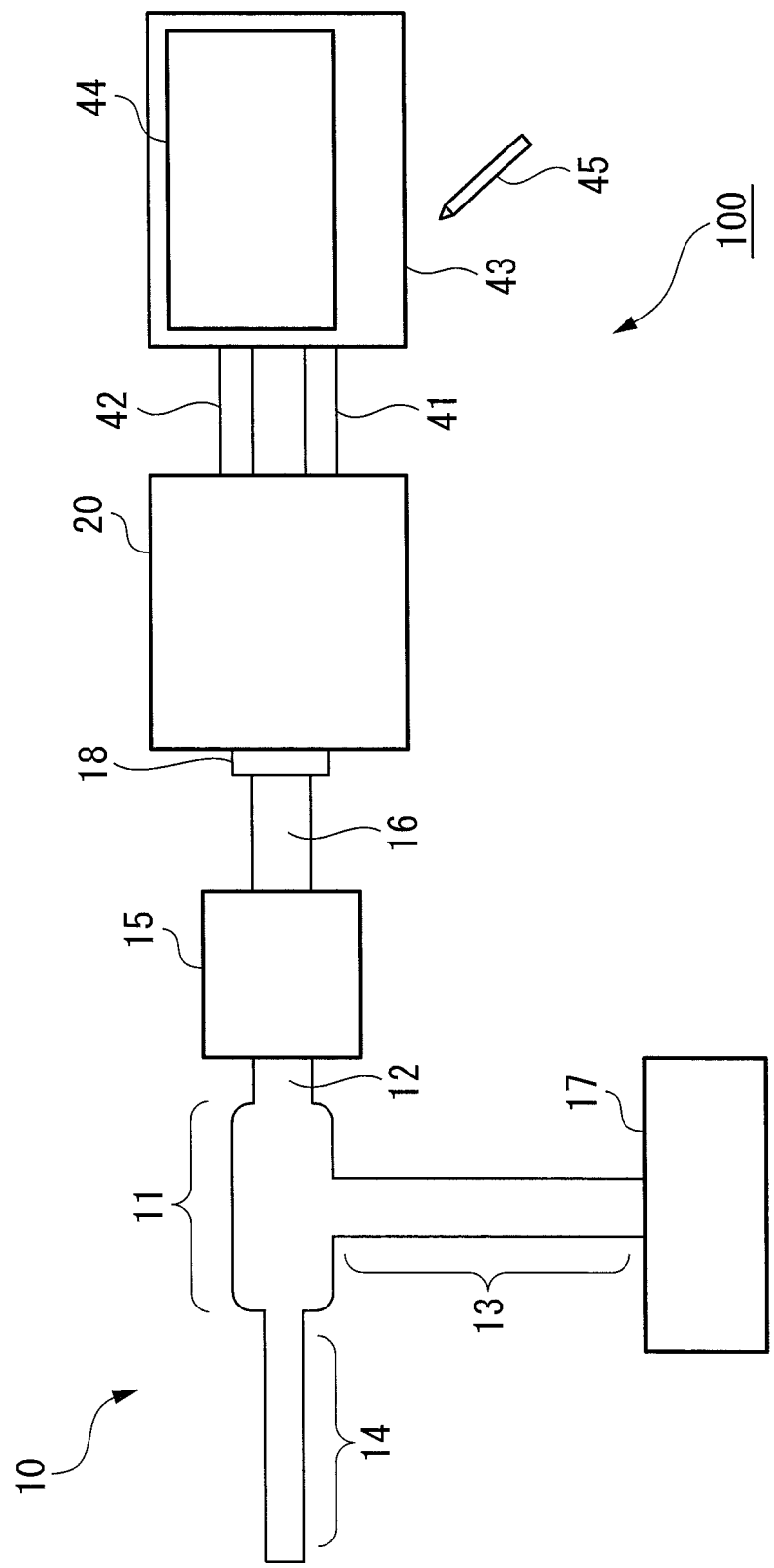
FIG. 1 is an overall schematic diagram of an endoscope system according to an embodiment of the present invention.

As shown in FIG. 1, the endoscope system 100 includes an endoscope 10 including an elongated insertion part 14. The endoscope 10 has a handle 11, and also has an eyepiece 12 at one end thereof. The handle 11 also has a light guide cable 13 extending therefrom and connected to a light source device (illumination light source) 17. Thus, light emitted from the light source device 17 is guided to the distal end of the insertion part 14 of the endoscope 10, thereby irradiating a subject.

The eyepiece 12 has a connection adaptor 15, which is connected to a control unit 20 through an image transmission cable 16 via a connection connector 18. Thus, image data acquired by the endoscope 10 is transmitted through the image transmission cable 16 to the control unit 20. The transmitted image data is subjected to image processing in the control unit 20, is transmitted through a monitor cable 41 to a monitor (image-displaying section) 43, and is displayed on a monitor screen 44.

The monitor screen 44 is a touch screen functioning as input means for inputting an instruction, such as for selecting a biopsy region, to the control unit 20. The user performs input operations on the monitor screen 44 by using a touch pen 45. The input information is transmitted through a touch screen cable 42 to the control unit 20, which processes the information.

Next, the detailed configuration of the fluoroscopy system 1 of this embodiment and the display on the monitor screen will be described using FIGS. 2 to 10.

Figure 2:
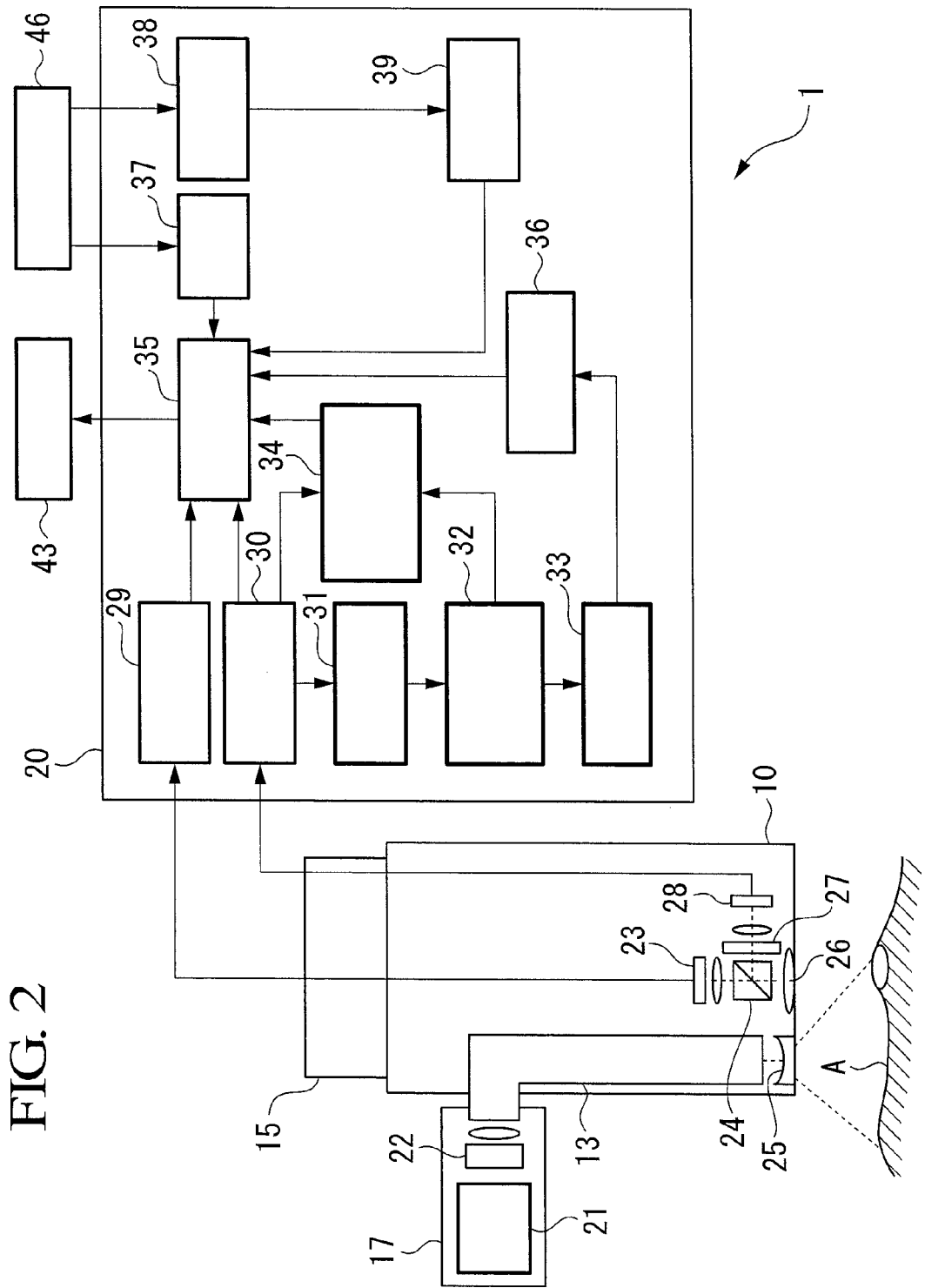
FIG. 2 is a functional block diagram of a fluoroscopy system according to a first embodiment of the present invention.
Figure 3:
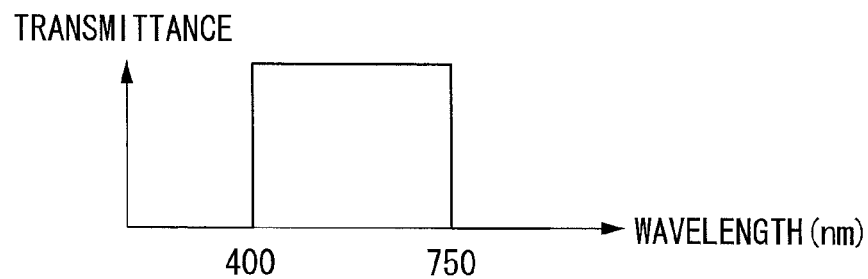
FIG. 3 shows a graph illustrating the transmittance of an excitation-light-pass filter in FIG. 2.

As shown in FIG. 2, the light source device 17 accommodates a xenon lamp (Xe lamp) 21 and a wavelength selection filter 22. The Xe lamp 21 emits white light and excitation light. The light emitted from the Xe lamp 21 passes through the wavelength selection filter 22, which allows only white light and excitation light in set wavelength ranges to pass therethrough. Specifically, as shown in FIG. 3, the wavelength selection filter 22 transmits light in the wavelength range of 400 to 750 nm and reflects light in the other wavelength range.

As shown in FIG. 2, the endoscope 10 accommodates a light guide cable 13, a white-light color CCD 23, a splitter 24, an illumination optical system 25, an image-acquisition optical system 26, an excitation-light-cut filter 27, and a fluorescence monochrome CCD 28.

The white light and excitation light emitted from the light source device 17 are guided through the light guide cable 13 in the endoscope 10 to the illumination optical system 25, which is disposed at the distal end of the endoscope 10, thereby irradiating a subject A. As the white light irradiates the subject A, the light reflected from the subject A enters the image-acquisition optical system 26, which is disposed at the distal end of the endoscope 10. As the excitation light irradiates the subject A, fluorescence is emitted from the subject A and enters the image-acquisition optical system 26.

The splitter 24 transmits the light reflected from the subject A and reflects the fluorescence emitted from the subject A. This property allows the splitter 24 to separate the reflected light and the fluorescence entering the image-acquisition optical system 26. A splitter that reflects light at wavelengths longer than the wavelength of the excitation light is used because the wavelength of the fluorescence is shifted to wavelengths longer than the wavelength of the excitation light.

Figure 4:
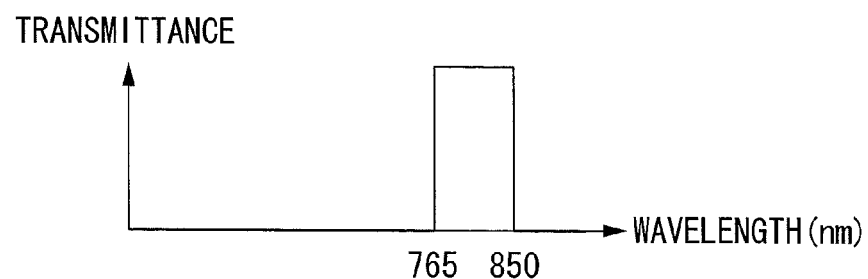
FIG. 4 shows a graph illustrating the transmittance of an excitation-light-cut filter in FIG. 2.

The excitation-light-cut filter 27 is a filter for removing the excitation light (reflected light) from the fluorescence. Specifically, as shown in FIG. 4, the excitation-light-cut filter 27 transmits light in the wavelength range of 765 to 850 nm.

The fluorescence passing through the excitation-light-cut filter 27 is completely separated from the excitation light (reflected light), and the separated fluorescence is detected by the fluorescence monochrome CCD 28. Because of the weakness of the separated fluorescence, the fluorescence monochrome CCD 28 used has a higher sensitivity than the white-light color CCD 23. The fluorescence image data detected by the fluorescence monochrome CCD 28 is transmitted through the image transmission cable 16 to a fluorescence-image generating section 30 in the control unit 20.

On the other hand, the light reflected from the subject A and passing through the splitter 24 is detected by the white-light color CCD 23. The white-light image data detected by the white-light color CCD 23 is transmitted through the image transmission cable 16 to a white-light-image generating section 29 in the control unit 20.

As shown in FIG. 2, the control unit 20 includes the following functions: the white-light-image generating section 29, the fluorescence-image generating section 30, an intensity-distribution generating section 31, a peak-detecting section 32, a peak-count comparing section (peak-count calculating section) 33, a region-extracting section 34, an image-combining section 35, a button-generating section 36, a mode-switching section 37, a selected-biopsy-position memory 38, and a pointer-generating section 39. Additionally, the control unit 20 is connected to the monitor 43 and to an input section (position-designating section) 46 that transmits an input signal to the control unit 20 when the monitor 43 is operated. As shown in FIG. 1, the input section 46 is the monitor screen 44 (touch screen).

The white-light-image generating section 29 generates a white-light image from the white-light image data detected by the white-light color CCD 23.

The fluorescence-image generating section 30 generates a fluorescence image from the fluorescence image data detected by the fluorescence monochrome CCD 28.

The fluorescence image generated by the fluorescence-image generating section 30 is transmitted to the image-combining section 35, the region-extracting section 34, and the intensity-distribution generating section 31. On the other hand, the white-light image generated by the white-light-image generating section 29 is transmitted to the image-combining section 35.

Figure 5B:
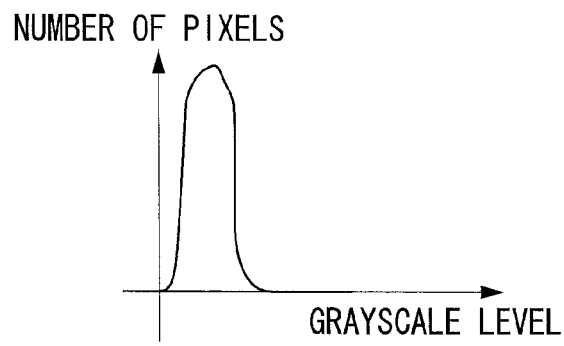
FIG. 5B shows a graph illustrating the image examined under the fluorescence endoscope in FIG. 2 in a normal condition, showing a histogram.
Figure 6A:
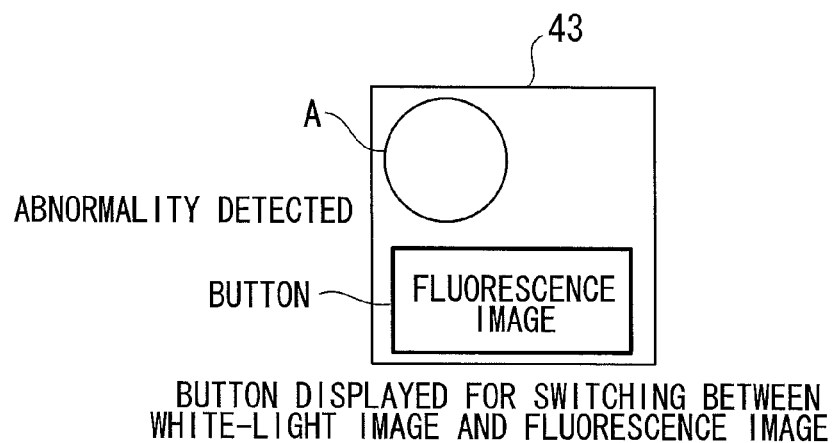
FIG. 6A is a diagram illustrating an image examined under the fluorescence endoscope in FIG. 2 upon detection of an abnormality, showing an example of a screen display.
Figure 6B:
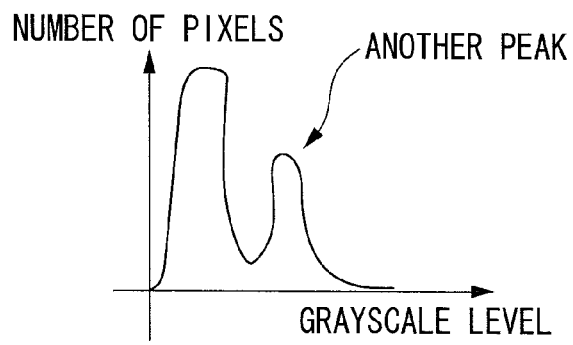
FIG. 6B shows a graph illustrating the image examined under the fluorescence endoscope in FIG. 2 upon detection of an abnormality, showing a histogram.

The intensity-distribution generating section 31 generates a fluorescence intensity distribution of the pixels of the fluorescence image generated by the fluorescence-image generating section 30. Specifically, the intensity-distribution generating section 31 generates a histogram based on the received fluorescence image. This histogram, as shown in FIGS. 5B and 6B, shows the distribution of the grayscale levels of the pixels and the numbers of pixels at the respective grayscale levels.

The histogram thus generated is transmitted to the peak-detecting section 32.

The peak-detecting section 32 detects fluorescence-intensity peaks in the fluorescence intensity distribution generated by the intensity-distribution generating section 31. Specifically, the peak-detecting section 32 executes peak detection on the histogram to detect the peak count and the grayscale levels at the peaks. The grayscale levels thus detected are transmitted to the region-extracting section 34, whereas the peak count is transmitted to the peak-count comparing section 33.

The peak-count comparing section 33 determines whether the peak count received from the peak-detecting section 32 is 1, or 2 or more. If the subject A under examination is normal, a single large peak appears in the lower grayscale range, as shown in FIG. 5B. Otherwise, if there is an affected area in the examination field of view, a region of high fluorescence intensity is present in the fluorescence image, and a new peak appears in the higher grayscale range in addition to the peak in the lower grayscale range, as shown in FIG. 6B.

Figure 5A:
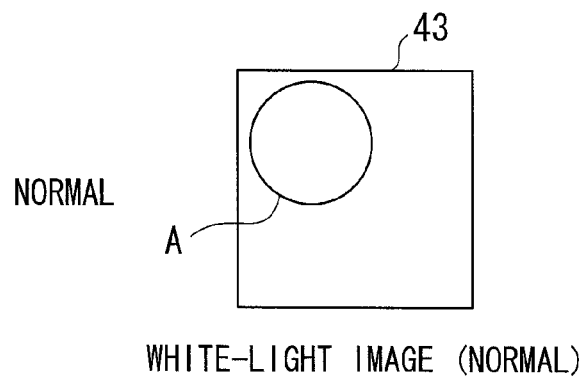
FIG. 5A is a diagram illustrating an image examined under a fluorescence endoscope in FIG. 2 in a normal condition, showing an example of a screen display.

If the peak count is 1 or less, the peak-count comparing section 33 determines that there is no affected area in the field of view and displays the white-light image on the monitor 43, as shown in FIG. 5A. Otherwise, if the peak count is 2 or more, the peak-count comparing section 33 determines that it has detected a signal indicating the presence of an affected area and transmits to the button-generating section 36 an instruction for generating a button for prompting the user to switch to the fluorescence image on the monitor 43. The button generated by the button-generating section 36 is transmitted to the image-combining section 35, which combines the button with the white-light image on the monitor 43, as shown in FIG. 6A.

Touching the button on the monitor 43 causes the input section 46 to transmit an input signal through the touch screen cable 42 to the mode-switching section 37 in the control unit 20. The mode-switching section 37 transmits an instruction for switching between the two modes, namely, the white-light image and the fluorescence image, to the image-combining section 35, which switches from the white-light image to the fluorescence image on the monitor 43.

Figure 7A:
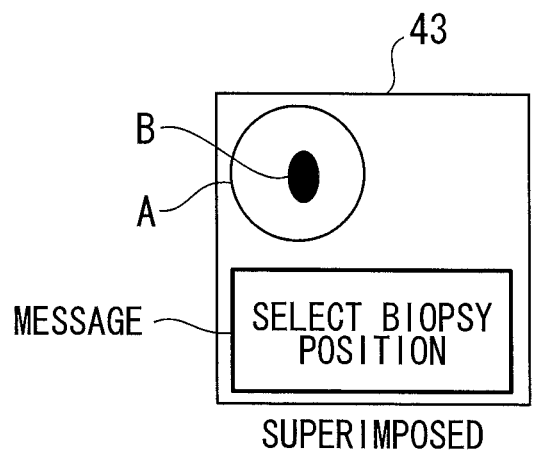
FIG. 7A is a diagram illustrating an image on which a superimposition image is superimposed with the fluorescence endoscope in FIG. 2, showing an example of a screen display.
Figure 7B:
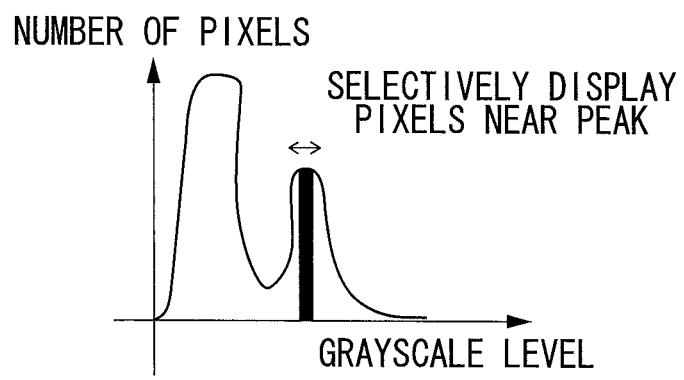
FIG. 7B shows a graph illustrating the image on which the superimposition image is superimposed with the fluorescence endoscope in FIG. 2, showing a histogram.

The region-extracting section 34 receives the grayscale levels at the peaks detected in the histogram, as shown in FIG. 7B, by the peak-detecting section 32. For the peaks detected, the region-extracting section 34 superimposes a display representing a region B including pixels having the fluorescence intensity at the second peak from the lower grayscale side by, for example, superimposition processing, as shown in FIG. 7A.

The image-combining section 35 combines the image superimposed by the region-extracting section 34, the white-light image generated by the white-light-image generating section 29 or the fluorescence image generated by the fluorescence-image generating section 30, a pointer, described later, generated by the pointer-generating section 39, and the button generated by the button-generating section 36.

The monitor 43 displays the combined image generated by the image-combining section 35. The monitor 43 may also display a message prompting the user to select a biopsy position, as shown in FIG. 7A.

Figure 9:
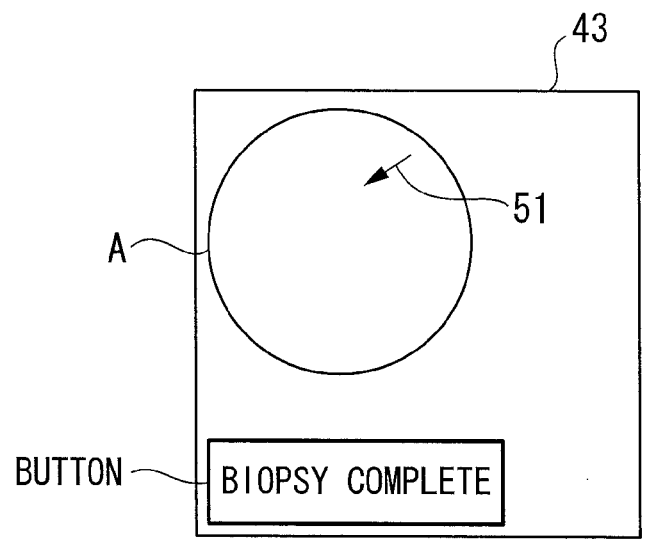
FIG. 9 is an example of a screen display on which a pointer is superimposed with the fluorescence endoscope in FIG. 2.

As shown in FIG. 7A, when the user checks the image displayed on the monitor 43 and selects the region where biopsy is to be performed from the superimposed region B on the touch screen, the input section 46 transmits selected-region-position information through the touch screen cable 42 to the control unit 20, which stores the information in the selected-biopsy-position memory 38. The selected-region-position information is transmitted to the pointer-generating section 39, which generates a pointer indicating a recommended optimum biopsy position. The information for the pointer is transmitted to the image-combining section 35, which, as shown in FIG. 9, superimposes a pointer 51 indicating the optimum biopsy position on the white-light image displayed on the monitor 43.

The operation of the fluoroscopy system thus configured will now be described with reference to the flowchart shown in FIG. 8.

Upon starting examination of an affected area using the fluoroscopy system 1 of this embodiment, a white-light image is acquired from light reflected from the subject A (step S1), and a fluorescence image is acquired from fluorescence emitted from the subject A (step S2).

The white-light image is displayed on the monitor 43, as shown in FIG. 5A, and the user examines the white-light image (step S3). The fluorescence image that has been acquired is not displayed on the monitor 43, although the grayscale levels and the numbers of pixels are counted, and the peak count is always detected (step S4).

A determination is made as to whether the peak count thus detected is 1, or 2 or more (step S5), and if the peak count is 2 or more, as shown in FIG. 6B, it is determined that there is a possible affected area in the field of view under examination (step S6).

In this manner, the peaks in the histogram are counted to detect an affected area, and if the peak count is 2 or more, as shown in FIG. 6A, a button for prompting the user to switch to the fluorescence image is displayed on the monitor 43 in addition to the white-light image being displayed (step S7).

If this button (display-mode changeover switch) is not touched, control returns to the start of the flowchart, and it is determined again whether there is an affected area in the examination field of view (step S8). Otherwise, if the changeover switch is touched, the display is switched from the white-light image to the fluorescence image, and a superimposed display screen in which the high-fluorescence-intensity region B of the fluorescence image is superimposed on the fluorescence image is displayed on the monitor 43, as shown in FIG. 7A (step S9).

The high-fluorescence-intensity region B, as shown in FIG. 7B, means a region including pixels near the grayscale level at the peak in the histogram. In this embodiment, the width of grayscale levels near the peak is set in advance, and pixels having grayscale levels within that width are superimposed.

If the user determines that biopsy is needed from the superimposed fluorescence image, he or she selects the region where biopsy is to be performed from the superimposed portion on the monitor 43 (touch screen) using the touch pen 45 (step S10).

A timer monitors whether the region where biopsy is to be performed has been selected within a predetermined period of time, and if the region is not selected within, for example, 15 seconds, it is determined that the user has determined that biopsy is not needed, and control returns to the start. The preset time of the timer is variable. Instead of using a timer, it is possible to enable the display to be switched from the superimposed image back to the white-light image by keeping the display-switching button on the monitor 43.

If the region where biopsy is to be performed is selected, the display on the monitor 43 is switched from the fluorescence image to the white-light image (step S11). As shown in FIG. 9, the white-light image displayed is a white-light image having the pointer 51, which indicates a point best suited for biopsy in the possible affected area.

Figure 10:
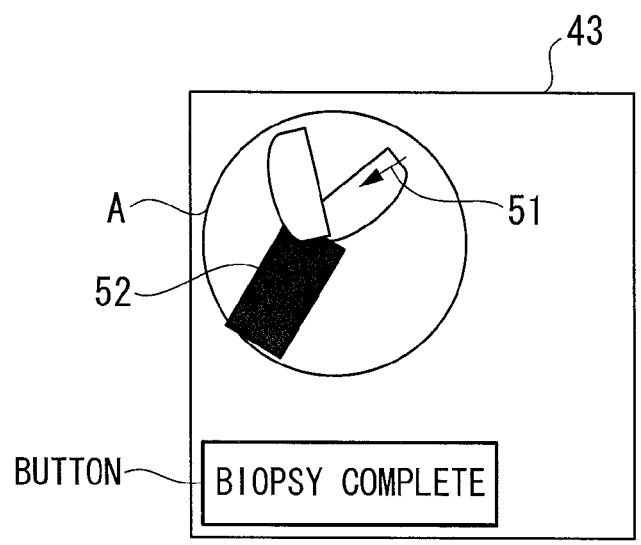
FIG. 10 is an example of a screen display on which a pointer is superimposed with the fluorescence endoscope in FIG. 2.

As shown in FIG. 10, this pointer 51 is always displayed in the foreground so that it is not hidden during the biopsy by, for example, forceps 52 occupying most of the image field of view. The user performs the biopsy by referring to the pointer 51 as the target position.

When the biopsy is complete, a biopsy complete button shown in FIGS. 9 and 10 is touched to return the flow to the start of the flowchart (step S12). Otherwise, if the biopsy complete button is not touched, the white-light image having the pointer 51 indicating the biopsy point is always displayed.

In the fluoroscopy system 1 according to this embodiment, as discussed above, the intensity-distribution generating section 31 generates a fluorescence intensity distribution of the pixels of the fluorescence image, and the peak-detecting section 32 detects fluorescence-intensity peaks in the fluorescence intensity distribution. If the peak count is 1, the peak-count comparing section 33 determines that the entire area on the screen is normal, and if the peak count is 2 or more, the peak-count comparing section 33 determines that there is an affected area on the screen and transmits an instruction to the button-generating section 36 to display a button, so that the screen display can be switched from the white-light image to the fluorescence image. The image-combining section 35 generates a combined image by superimposing, on the fluorescence image, a display representing the region B including the pixels having the fluorescence intensity at the peak, and the combined image is displayed on the monitor 43.

The region B including the pixels having the fluorescence intensity at the peak is likely to be an affected area. Displaying the region B on the fluorescence image by superimposition allows the user to easily locate the affected area for proper inspection and treatment of the affected area.

Further, the position where biopsy is to be performed in the combined image can be designated on the monitor 43 (touch screen) to display its positional information in the form of the pointer 51 on the white-light image. This allows treatment, such as biopsy, at the designated position while viewing the white-light image on which the display (pointer 51) identifying the designated position is superimposed, thereby improving the accuracy of inspection and treatment of the affected area.

Whereas this embodiment always displays the white-light image and switches to the fluorescence image in response to an instruction when necessary, it is also possible to always display the white-light image and the fluorescence image side-by-side on the display screen. In this case, touching the display-mode changeover switch causes the region noted as requiring biopsy to be displayed on the fluorescence image without changing the white-light image. When the position where biopsy is to be performed is selected on the fluorescence image, the position is indicated by the pointer 51 on the white-light image.

Second Embodiment

Figure 11:
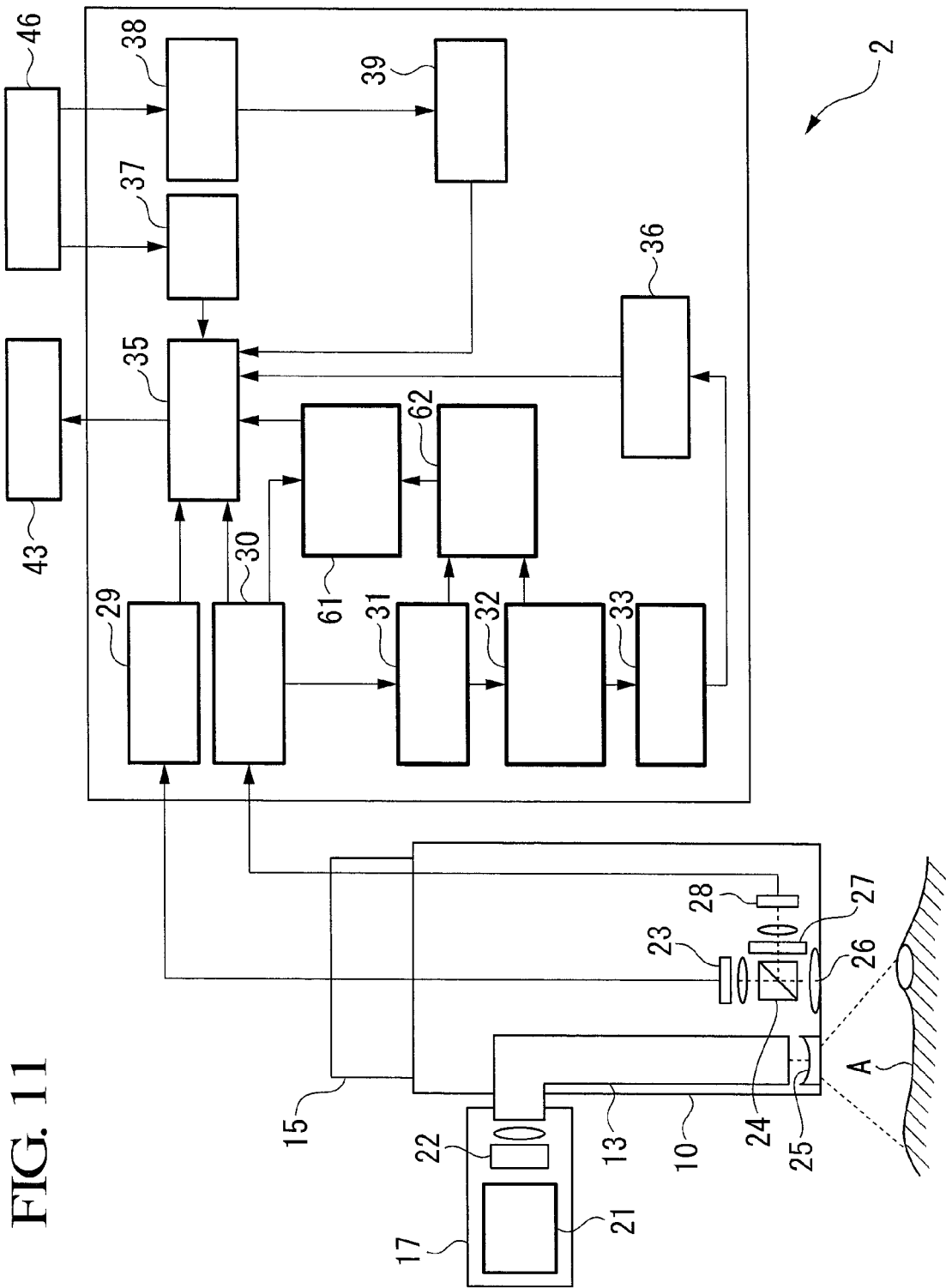
FIG. 11 is a functional block diagram of a fluoroscopy system according to a second embodiment of the present invention.
Figure 12A:
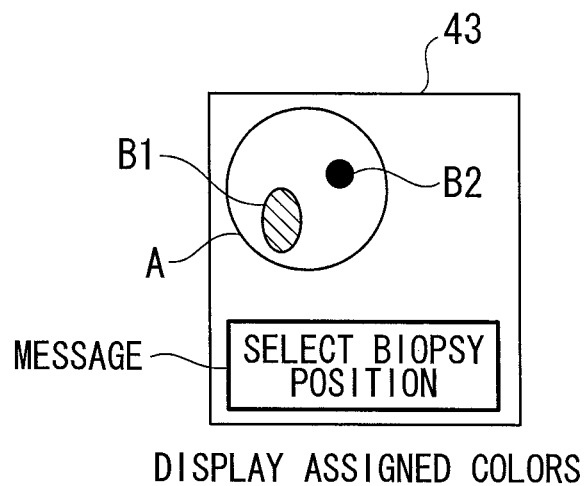
FIG. 12A is a diagram illustrating an image on which colored regions are superimposed with a fluorescence endoscope in FIG. 11, showing an example of a screen display.

A fluoroscopy system 2 according to a second embodiment of the present invention will now be described using FIGS. 11 to 13. FIG. 11 is a functional block diagram of the fluoroscopy system 2 according to the second embodiment, which is similar to the fluoroscopy system 1 according to the first embodiment except for the processing performed on the fluorescence image in the control unit 20. The second embodiment is identical to the first embodiment in the process up to the generation of the white-light image and the fluorescence image, but is different from the first embodiment in the processing for displaying the high-fluorescence-intensity region and also in the display for selecting the biopsy region on the monitor 43.

The fluorescence image generated by the fluorescence-image generating section 30 is transmitted to the image-combining section 35, a coloring section 61, and the intensity-distribution generating section 31. On the other hand, the white-light image generated by the white-light-image generating section 29 is transmitted to the image-combining section 35.

The intensity-distribution generating section 31 generates a histogram based on the received fluorescence image. This histogram, as shown in FIG. 12B, shows the grayscale levels of the pixels and the numbers of pixels at the respective grayscale levels.

The histogram thus generated is transmitted to the peak-detecting section 32 and a color-setting section 62. The peak-detecting section 32 executes peak detection on the histogram to obtain the peak count and the grayscale levels at the peaks. The grayscale levels at the peaks thus obtained are transmitted to the color-setting section 62, whereas the peak count is transmitted to the peak-count comparing section 33.

Figure 12B:
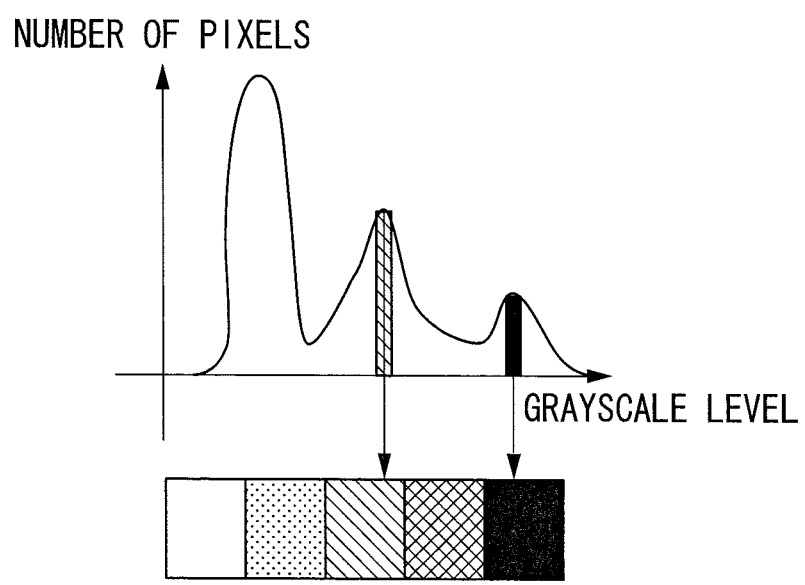
FIG. 12B shows a graph illustrating the image on which the colored regions are superimposed with the fluorescence endoscope in FIG. 11, showing a histogram.
Figure 13:
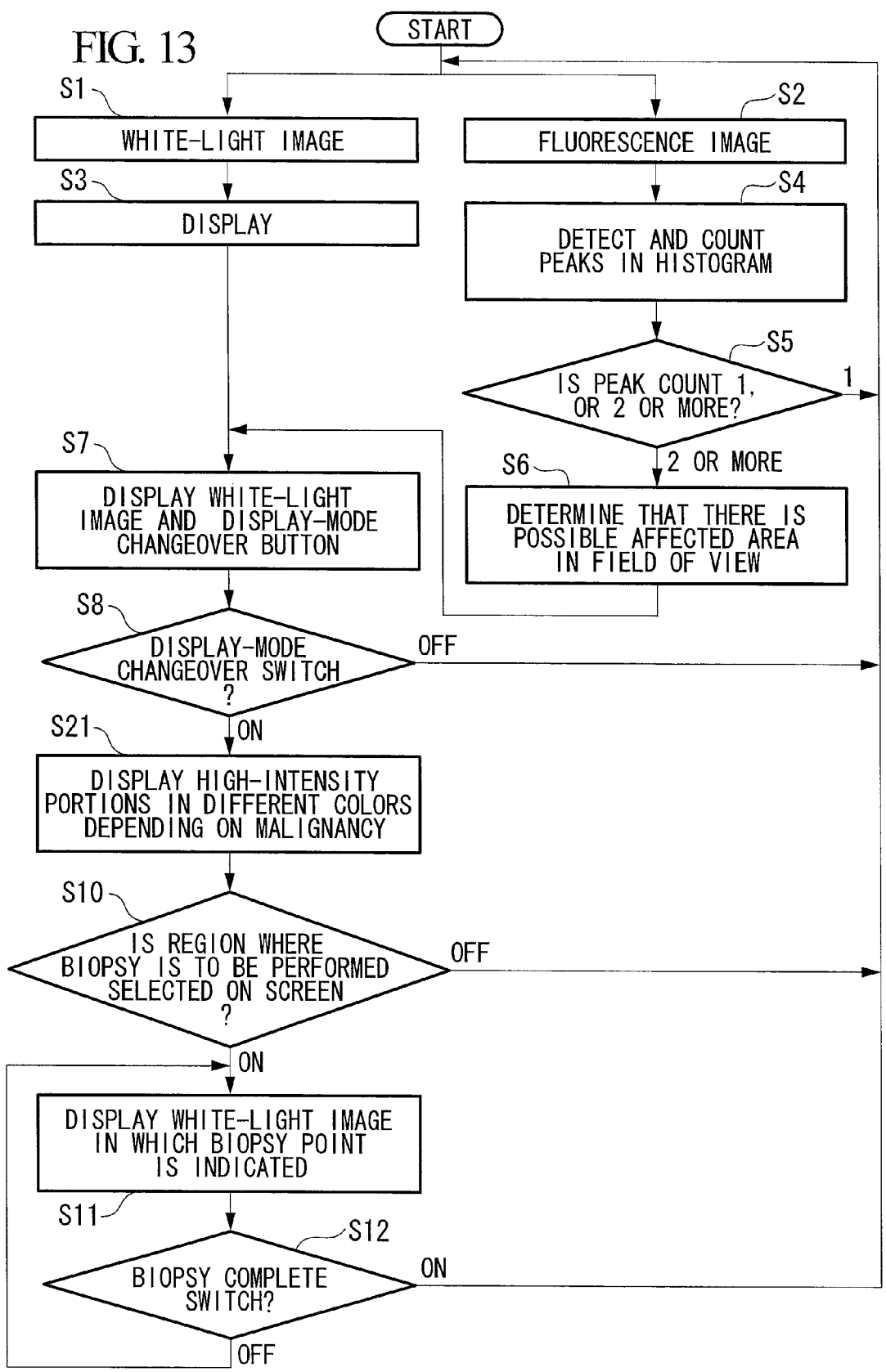
FIG. 13 is a flowchart showing a process executed by the fluorescence endoscope in FIG. 11.

As shown in FIG. 12B, the color-setting section 62 stores colors assigned to grayscale levels in advance. The number of classes of grayscale levels for assignment and the colors thereof are variable. As shown in FIG. 11, the color-setting section 62 receives the histogram generated from the fluorescence image from the intensity-distribution generating section 31 and the grayscale levels at the peaks from the peak-detecting section 32.

As shown in FIG. 12B, the color-setting section 62 determines to what colors the grayscale levels at the peaks detected this time belong, from among the colors assigned to grayscale levels in advance, and sets the colors. That is, different colors are set to different grayscale levels at the peaks so that possible affected areas can be displayed in different colors on the monitor 43. Because the difference in color results from the difference in grayscale level, i.e., from the difference in fluorescence intensity, the affected areas can be displayed so that the difference in malignancy can be easily visualized using color.

The pixels near the grayscale levels at the peaks are also selected from the histogram. The grayscale levels at the histogram peaks, the colors set for the peaks, and the information about the pixels near the peaks are transmitted to the coloring section 61.

Based on the fluorescence image received from the fluorescence-image generating section 30, the coloring section 61 generates a display representing the pixels at and near the grayscale levels at the peaks in the image, using the colors set by the color-setting section 62. The display is transmitted to the image-combining section 35.

As in the first embodiment, the peak-count comparing section 33 determines whether the received peak count is 1, or 2 or more. If the peak count is 1 or less, it determines that there is no affected area in the field of view and displays the white-light image on the monitor 43. Otherwise, if the peak count is 2 or more, the peak-count comparing section 33 determines that it has detected a signal indicating an affected area and transmits to the button-generating section 36 an instruction for generating a button for prompting the user to switch to the fluorescence image on the monitor 43.

The button generated by the button-generating section 36 is transmitted to the image-combining section 35, which combines the button with the white-light image on the monitor 43. Touching the button on the monitor 43 causes the input section 46 to transmit an input signal through the touch screen cable 42 to the mode-switching section 37 in the control unit 20. The mode-switching section 37 transmits an instruction for switching between the two modes, namely, the white-light image and the fluorescence image, to the image-combining section 35, which switches from the white-light image to the fluorescence image on the monitor 43. The monitor 43 may also display a message prompting the user to select a biopsy position, as shown in FIG. 12A.

As shown in FIG. 12A, the fluorescence image thus displayed is an image combined with the display, generated by the coloring section 61, that represents the regions near the grayscale peaks in different colors depending on the grayscale levels of the fluorescence image. When the user checks this display, which visualizes the difference in malignancy using color, on the monitor 43 and selects the region where biopsy is to be performed from regions B1 and B2 represented in different colors on the touch screen, the input section 46 transmits selected-region-position information through the touch screen cable 42 to the control unit 20, which stores the information in the selected-biopsy-position memory 38.

The selected-region-position information is transmitted to the pointer-generating section 39, which generates a pointer indicating a recommended optimum biopsy point. The information for the pointer is transmitted to the image-combining section 35, which, as shown in FIG. 9, superimposes a pointer 51 indicating the optimum biopsy position on the white-light image on the monitor 43.

The operation of the fluoroscopy system 2 thus configured will now be described with reference to the flowchart shown in FIG. 13.

The fluoroscopy system 2 of this embodiment executes similar processing to the fluoroscopy system 1 of the first embodiment until the display-mode changeover switch is turned on. That is, while the white-light image is displayed and examined, the fluorescence image is not displayed on the monitor 43, although the grayscale levels and the numbers of pixels are counted, and the peak count is always detected (steps S1 to S7).

If the button (display-mode changeover switch) is not touched, control returns to the start of the flowchart, and it is determined again whether there is an affected area in the examination field of view (step S8). Otherwise, if the changeover switch is touched, the display is switched from the white-light image to the fluorescence image, and an image combined with the display representing the high-fluorescence-intensity regions B1 and B2 in different colors depending on malignancy (the grayscale levels at the peaks) is displayed, as shown in FIG. 12A (step S21). The high-fluorescence-intensity regions mean regions including pixels near the grayscale levels at the peaks in the histogram.

If it is determined that biopsy is needed from the fluorescence image represented in different colors, the region where biopsy is to be performed on the monitor 43 is selected from the portions represented in different colors using the touch pen 45 (step S10). The subsequent process up to completion of biopsy (steps S11 and S12) is similar to the process in the first embodiment and is therefore not described herein.

As above, not only does the fluoroscopy system 2 of this embodiment detect a peak level from the histogram of the fluorescence image to detect an affected area with high fluorescence intensity and to display its position on the white-light image, as does the fluoroscopy system 2 of the first embodiment, but it also assigns a color depending on the difference in peak level. In this case, because the fluorescence intensity becomes higher as the malignancy of an affected area becomes higher, the representation of the difference in peak level by color allows the difference in malignancy to be represented by color. Thus, the user can easily recognize the difference in malignancy between a plurality of possible affected areas on the examination screen by color, thereby easily determining where biopsy should be performed.

Third Embodiment

Figure 14:
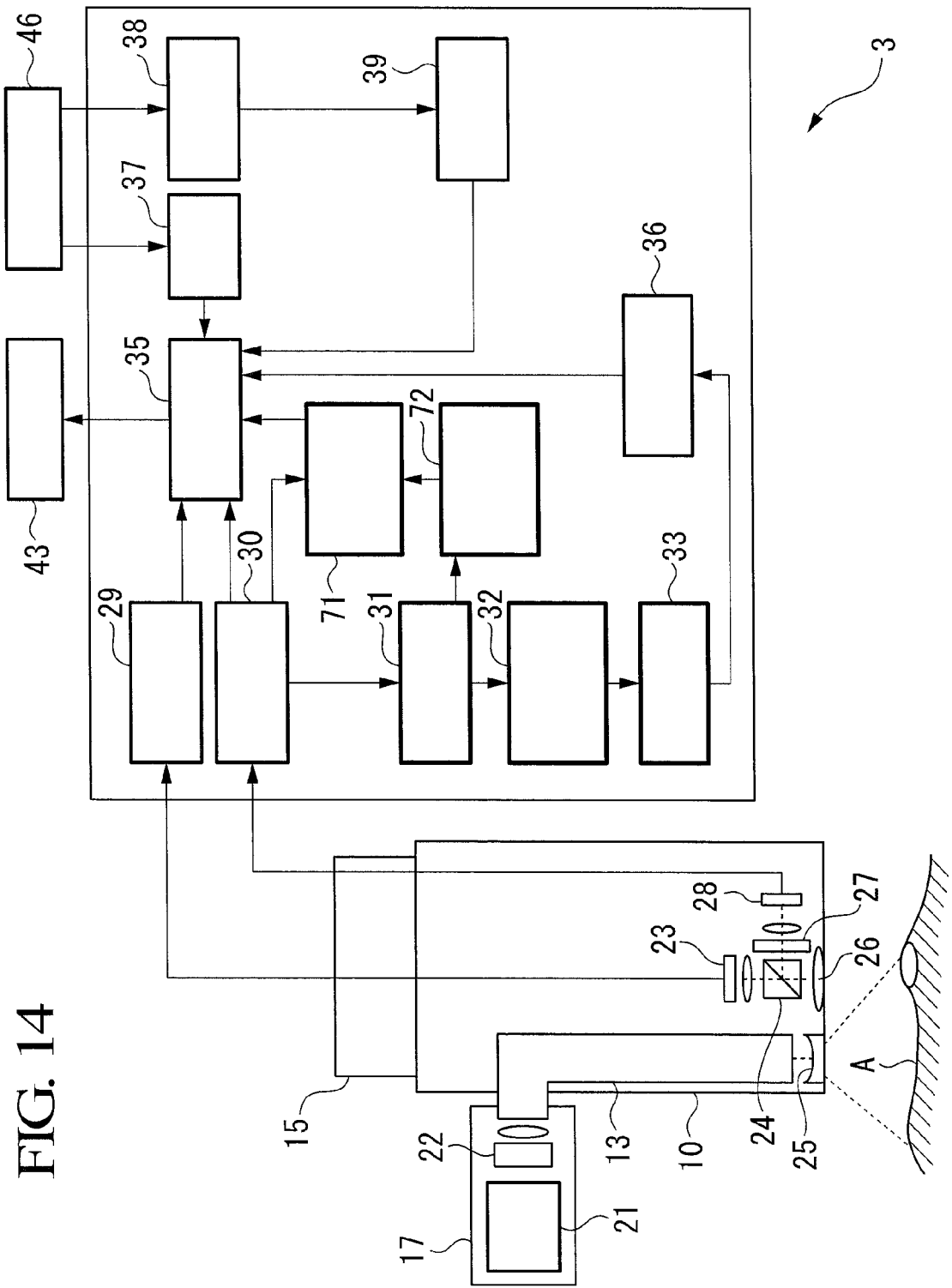
FIG. 14 is a functional block diagram of a fluoroscopy system according to a third embodiment of the present invention.
Figure 15A:
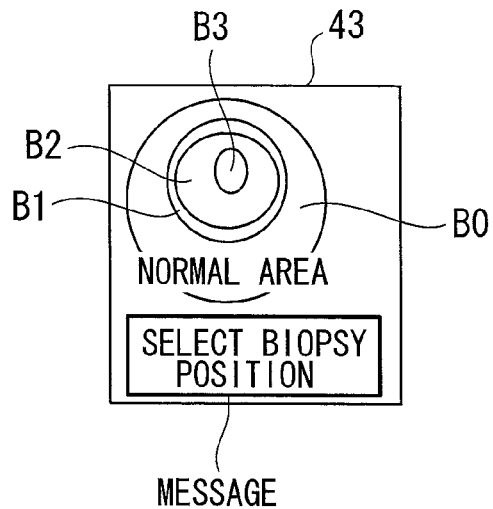
FIG. 15A is a diagram illustrating an image on which contours are superimposed with a fluorescence endoscope in FIG. 14, showing an example of a screen display.

A fluoroscopy system 3 according to a third embodiment of the present invention will now be described using FIGS. 14 to 16. FIG. 14 is a functional block diagram of the fluoroscopy system 3 according to this embodiment, which is similar to the first embodiment described above except for the processing performed on the fluorescence image in the control unit 20. This embodiment generates a white-light image and a fluorescence image, as in the above embodiments, but differs therefrom in the processing performed after generating the fluorescence image.

The fluorescence image generated by the fluorescence-image generating section 30 is transmitted to the image-combining section 35, a contour-displaying section 71, and the intensity-distribution generating section 31. On the other hand, the white-light image generated by the white-light-image generating section 29 is transmitted to the image-combining section 35.

The intensity-distribution generating section 31 generates a histogram based on the received fluorescence image. This histogram, as shown in FIG. 15B, shows the grayscale levels of the pixels and the numbers of pixels at the respective grayscale levels.

The histogram thus generated is transmitted to the peak-detecting section 32 and a range-setting section 72. The peak-detecting section 32 executes peak detection on the histogram to obtain the peak count and the grayscale levels at the peaks. The peak count thus obtained is transmitted to the peak-count comparing section 33.

Figure 15B:
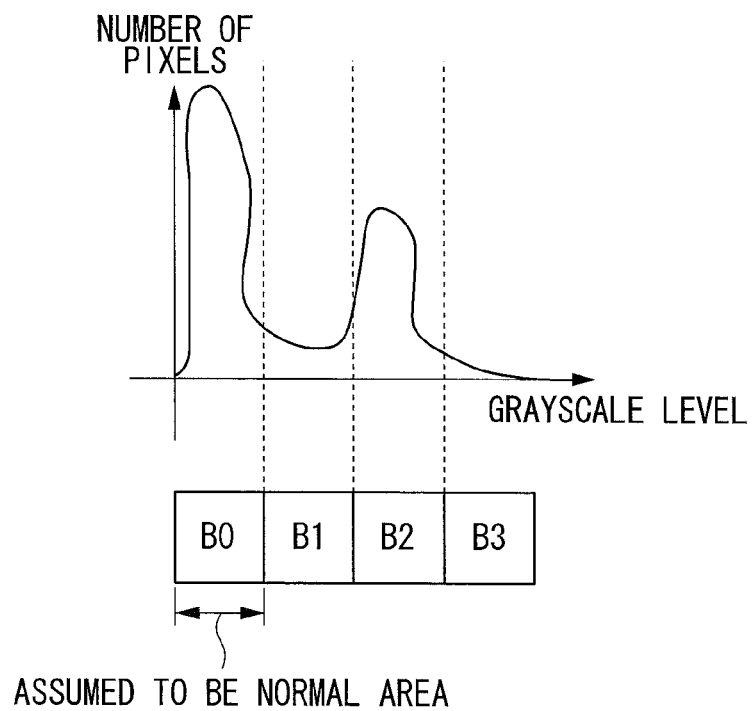
FIG. 15B shows a graph illustrating the image on which the contours are superimposed with the fluorescence endoscope in FIG. 14, showing a histogram.
Figure 16:
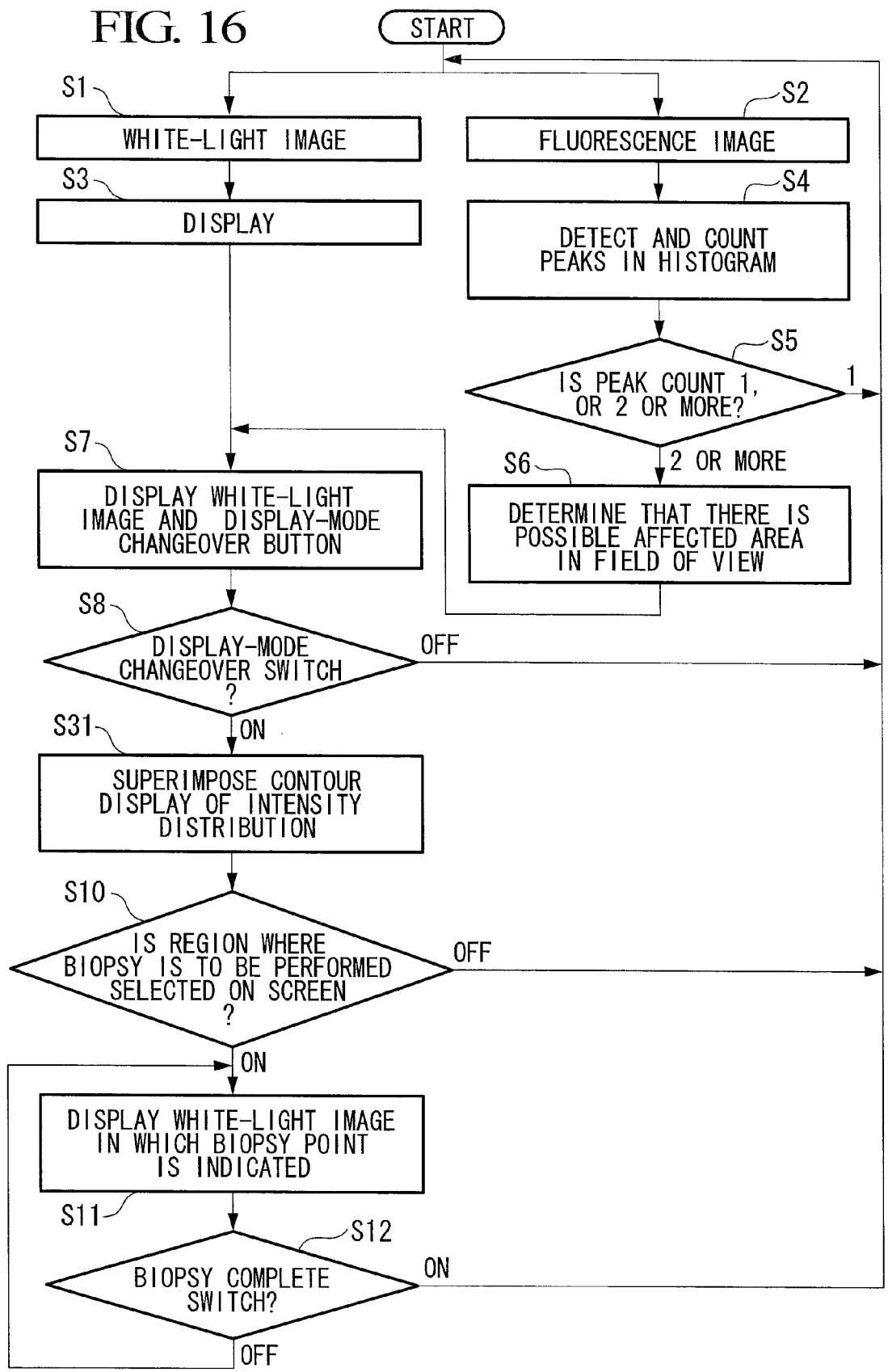
FIG. 16 is a flowchart showing a process executed by the fluorescence endoscope in FIG. 14.

As shown in FIG. 15B, the range-setting section 72 stores ranges, such as a range B0, a range B1, a range B2, etc., assigned to grayscale levels in advance. The number of ranges of grayscale levels for assignment is variable. An example where the grayscale levels are divided into four ranges, namely, B0 to B3, is described herein. The range B0, which is a region having the lowest fluorescence intensity, is assumed to be a normal area, where the fluorescence image is not superimposed on the white-light image.

As shown in FIG. 14, the range-setting section 72 receives the histogram generated from the fluorescence image from the intensity-distribution generating section 31. As shown in FIG. 15B, the range-setting section 72 determines to what ranges the individual grayscale levels belong, from among the grayscale ranges set in advance, and transmits the information about the ranges to which the individual grayscale levels are set to the contour-displaying section 71.

Based on the fluorescence image received from the fluorescence-image generating section 30, the contour-displaying section 71 determines what pixels in the image are located at the limits of the grayscale ranges set as above and generates a contour display for the portion corresponding to those pixels. The contour display thus generated is displayed on the white-light image, as shown in FIG. 15A.

This processing provides a contour display of fluorescence intensity, which allows the viewer to easily learn how the fluorescence intensity is distributed and where the fluorescence intensity is high in the fluoroscopy image so that he or she can easily determine the region where biopsy is to be performed.

As in the second embodiment, the regions separated by the contours can be represented in different colors depending on the grayscale levels.

As in the first embodiment, the peak-count comparing section 33 determines whether the received peak count is 1, or 2 or more. If the peak count is 1 or less, it determines that there is no affected area in the field of view and displays the white-light image on the monitor 43. Otherwise, if the peak count is 2 or more, the peak-count comparing section 33 determines that it has detected a signal indicating an affected area and transmits to the button-generating section 36 an instruction for generating a button for prompting the user to switch to the fluorescence image on the monitor 43.

The button generated by the button-generating section 36 is transmitted to the image-combining section 35, which combines the button with the white-light image on the monitor 43. Touching the button on the monitor 43 causes the input section 46 to transmit an input signal through the touch screen cable 42 to the mode-switching section 37 in the control unit 20. The mode-switching section 37 transmits an instruction for switching between the two modes, namely, the white-light image and the fluorescence image, to the image-combining section 35, which switches from the white-light image to the fluorescence image on the monitor 43. The monitor 43 may also display a message prompting the user to select a biopsy position, as shown in FIG. 15A.

The fluorescence image thus displayed is an image combined with a contour display of the fluorescence intensity distribution. When the user checks the fluorescence image combined with the contour display on the monitor 43 and selects the region where biopsy is to be performed on the monitor 43, the input section 46 transmits selected-region-position information through the touch screen cable 42 to the control unit 20, which stores the information in the selected-biopsy-position memory 38. The selected-region-position information is transmitted to the pointer-generating section 39, which generates a pointer indicating the position where biopsy is to be performed, which is transmitted to the image-combining section 35. Thus, a white-light image on which the pointer 51 indicating the position where biopsy is to be performed is superimposed is displayed on the monitor 43.

The operation of the fluoroscopy system 3 thus configured will now be described with reference to the flowchart shown in FIG. 16.

The fluoroscopy system 3 of this embodiment executes similar processing to the fluoroscopy systems of the above embodiments until the display-mode changeover switch is turned on. That is, while the white-light image is displayed and examined, the fluorescence image is not displayed on the monitor 43, although the grayscale levels and the numbers of pixels are counted, and the peak count is always detected (steps S1 to S7).

If the button (display-mode changeover switch) is not touched, control returns to the start, and it is determined again whether there is an affected area in the examination field of view (step S8). Otherwise, if the changeover switch is touched, the display is switched from the white-light image to the fluorescence image, and an image combined with a contour display of the fluorescence intensity distribution is displayed, as shown in FIG. 15A (step S31).

If it is determined that biopsy is needed from the fluorescence image combined with the contour display of the fluorescence intensity distribution, the portion where biopsy is to be performed is selected on the monitor 43 using the touch pen 45 (step S10). The subsequent process up to completion of biopsy (steps S11 and S12) is similar to the process in the above embodiments and is therefore not described herein.

As above, not only does the fluoroscopy system 3 of this embodiment detect a peak level from the histogram of the fluorescence image to display its position and to add color for ease of recognition of malignancy, as do the fluoroscopy systems of the above embodiments, but it also provides a straightforward contour display of the fluorescence intensity distribution for a high-intensity region.

Because the fluorescence intensity becomes higher as the malignancy of an affected area becomes higher, the portion having the highest fluorescence intensity in the high-fluorescence-intensity region is a position best suited for biopsy. A straightforward contour display of the fluorescence intensity distribution for the high-intensity region allows the user to easily determine where the fluorescence intensity is highest in the high-fluorescence-intensity region displayed on the examination screen and where is best suited for biopsy.

Fourth Embodiment

Figure 17:
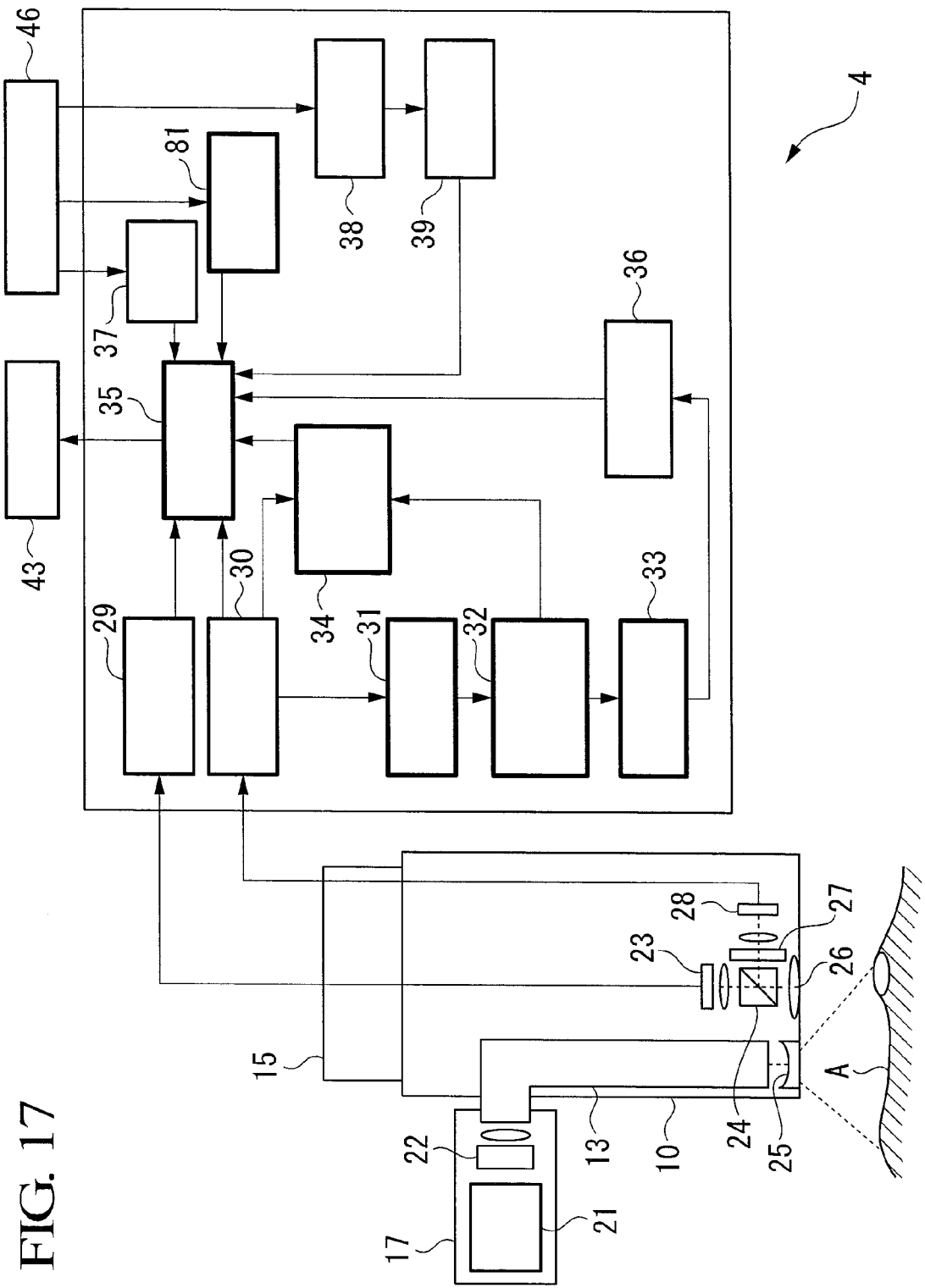
FIG. 17 is a functional block diagram of a fluoroscopy system according to a fourth embodiment of the present invention.

A fluoroscopy system 4 according to a fourth embodiment of the present invention will now be described using FIGS. 17 to 19. FIG. 17 is a functional block diagram of the fluoroscopy system 4 of this embodiment, which is similar to the fluoroscopy system 1 according to the first embodiment except for the processing performed on the fluorescence image in the control unit 20. This embodiment involves examination of an affected area, as in the above embodiments, but differs therefrom in that the image-combining section 35 has an image-enlarging function.

The fluorescence image generated by the fluorescence-image generating section 30 is transmitted to the image-combining section 35, the region-extracting section 34, and the intensity-distribution generating section 31. On the other hand, the white-light image generated by the white-light-image generating section 29 is transmitted to the image-combining section 35.

The fluorescence image transmitted to the region-extracting section 34 and the intensity-distribution generating section 31 is processed as in the first embodiment, and the region-extracting section 34 transmits information about a high-fluorescence-intensity region and superimposition information for representing that region to the image-combining section 35. The button-generating section 36 transmits information for an image-switching button and an enlarge button to the image-combining section 35.

Based on the information for the image-switching button received from the button-generating section 36, the image-combining section 35 combines the image-switching button with the white-light image on the monitor 43. Touching the image-switching button on the monitor 43 causes the input section 46 to transmit an input signal through the touch screen cable 42 to the mode-switching section 37 in the control unit 20. The mode-switching section 37 transmits an instruction for switching between the two modes, namely, the white-light image and the fluorescence image, to the image-combining section 35, which switches from the white-light image to the fluorescence image on the monitor 43.

Figure 18:
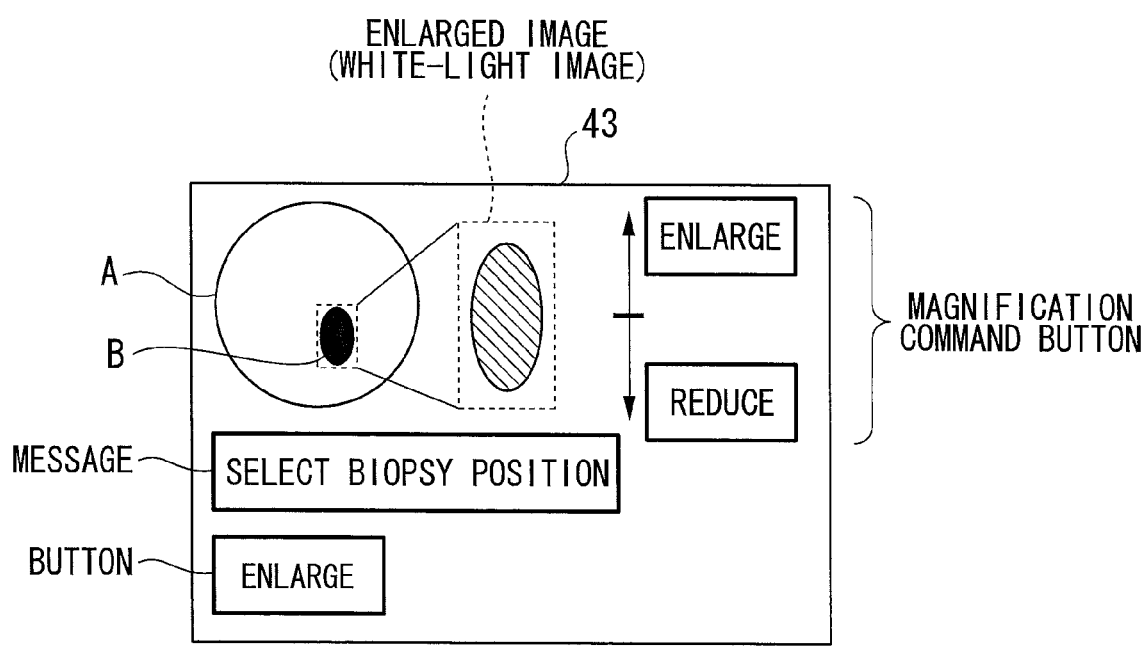
FIG. 18 is an example of a screen display on which an enlarged image is superimposed with a fluorescence endoscope in FIG. 17.
Figure 19:
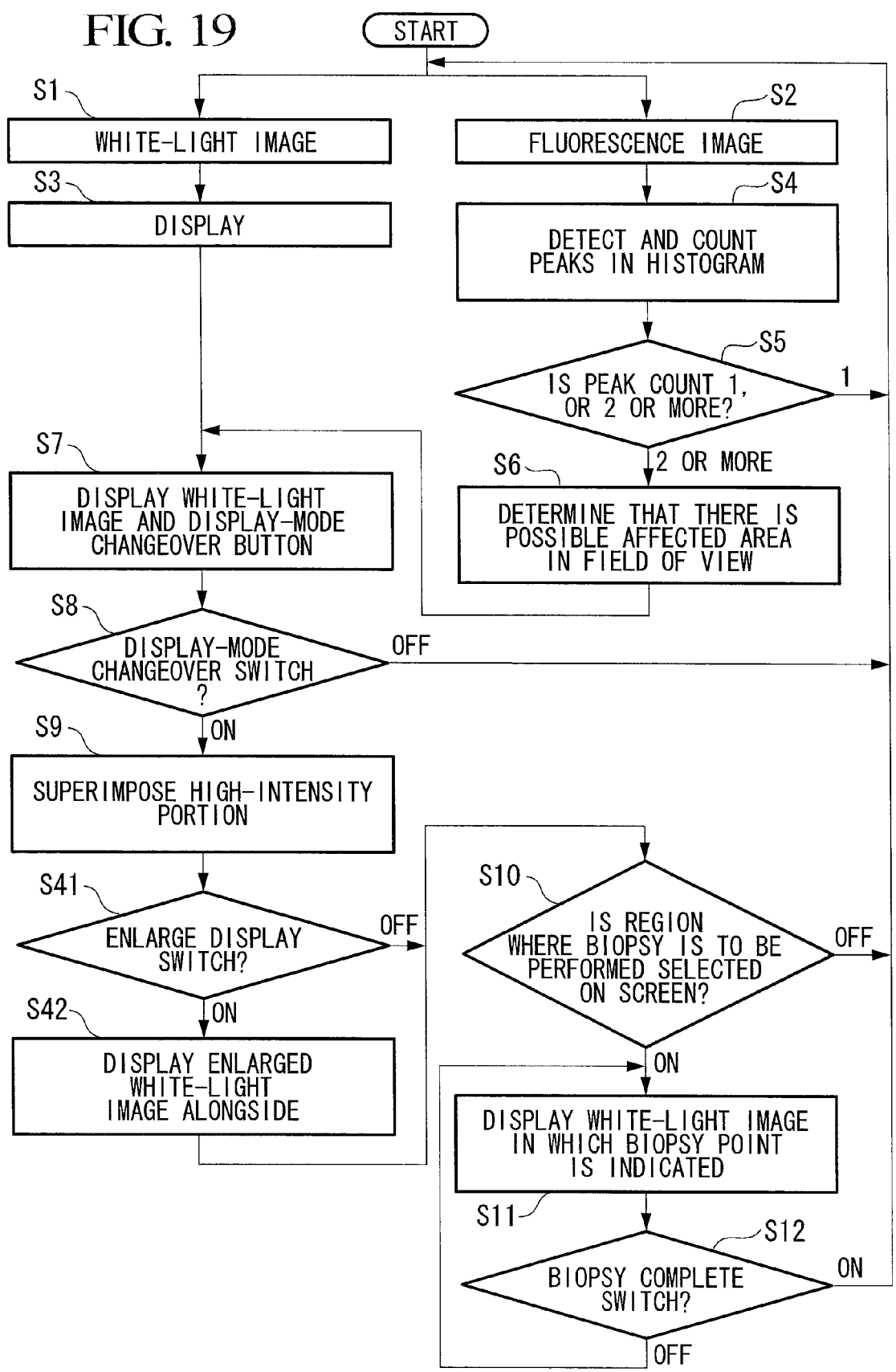
FIG. 19 is a flowchart showing a process executed by the fluorescence endoscope in FIG. 17.

As shown in FIG. 18, the screen thus displayed is a screen showing a superimposed fluorescence image, as in the first embodiment, with which the enlarge button generated by the button-generating section 36 is combined. Touching the enlarge button on the monitor 43 causes the input section 46 to transmit an input signal through the touch screen cable 42 to an enlarged-region memory 81 in the control unit 20. At the same time, an instruction for displaying a high-fluorescence-intensity region (superimposed region) B as a white-light image is transmitted to the image-combining section 35. The input section 46 functions as an area-setting section for designating the area to be enlarged by operating the monitor 43.

Based on the information about the high-fluorescence-intensity region B, the image-combining section 35 obtains a white-light-image region including pixels corresponding to the region B by trimming. The white-light image obtained by trimming is subjected to digital zoom processing, which assigns pixel data to a plurality of pixels on the monitor 43. The digitally, zoomed image is combined and displayed beside the fluorescence image, as shown in FIG. 18. The magnification of the digital zoom processing is variable, and a magnification suitable for examination of an affected area can be selected by touching an enlarge/reduce command button (magnification command button) displayed beside the enlarged image. The monitor 43 may also display a message prompting the user to select a biopsy position, as shown in FIG. 18.

Selecting the region where biopsy is to be performed on the monitor 43 via the touch screen causes the input section 46 to transmit selected-region-position information through the touch screen cable 42 to the control unit 20, which stores the information in the selected-biopsy-position memory 38. The selected-region-position information is transmitted to the pointer-generating section 39, which generates a pointer indicating the position where biopsy is to be performed, which is transmitted to the image-combining section 35. Thus, a white-light image in which the position where biopsy is to be performed is indicated is displayed on the monitor 43.

The region where biopsy is to be performed can be set on the touch screen either by selecting the enlarged high-fluorescence-intensity portion or by selecting the region from the entire image before enlargement.

The operation of the fluoroscopy system 4 thus configured will now be described with reference to the flowchart shown in FIG. 19.

The fluoroscopy system 3 of this embodiment executes similar processing to the fluoroscopy system 1 of the first embodiment until the display-mode changeover switch is turned on. That is, while the white-light image is displayed and examined, the fluorescence image is not displayed on the monitor 43, although the grayscale levels and the numbers of pixels are counted, and the peak count is always detected (steps S1 to S7).

If the button (display-mode changeover switch) is not touched, control returns to the start, and it is determined again whether there is an affected area in the examination field of view (step S8). Otherwise, if the changeover switch is touched, the display is switched from the white-light image to the fluorescence image, and a fluorescence image on which the high-fluorescence-intensity region is superimposed and with which the enlarge button is combined is displayed, as shown in FIG. 18 (step S9).

Touching the enlarge button causes an enlarged white-light image including the high-fluorescence-intensity region (superimposed region) to be displayed beside the fluorescence image (steps S41 and S42). If the enlarge button is not touched, the region where biopsy is to be performed is selected on the screen, or if the biopsy region is not selected, control returns to the start, as in the first embodiment (step S10).

While examining the enlarged white-light image of the high-fluorescence-intensity region displayed by touching the enlarge button, the user determines whether biopsy should be performed (step S42). The enlarged image provides information about the color, condition, and profile of the subject, thus providing more information for determining whether biopsy should be performed.

If it is determined that biopsy is needed, the region where biopsy is to be performed is selected on the monitor 43 (touch screen) using the touch pen 45 (step S10). The subsequent process up to completion of biopsy (steps S11 and S12) is similar to the process in the first embodiment and is therefore not described herein.

As above, not only does the fluoroscopy system 4 of this embodiment help to determine the biopsy position from the fluorescence image information, as do the fluoroscopy systems of the above embodiments, but it also helps to determine whether biopsy should be performed by providing an enlarged white-light image of a high-fluorescence-intensity region. Because a higher fluorescence intensity indicates an affected area with a higher malignancy, it could have a different color and profile from the surrounding environment in the white-light image. The white-light examination of the high-fluorescence-intensity region provides the user with more information for determining whether biopsy should be performed.

The enlarged white-light image of the high-fluorescence-intensity region provides the user with information about the profile and color of the affected area and the surrounding area, which allows him or her to easily determine where biopsy should be performed.

Whereas embodiments of the present invention have been described in detail above with reference to the drawings, the specific configuration thereof is not limited to those embodiments, but encompasses, for example, design changes within the spirit of the present invention.

For example, although the fluoroscopy system according to the present invention is applied to an endoscope system in the embodiments described above, it may also be applied to, for example, microscope systems.

In addition, although a high-fluorescence-intensity region is superimposed on a fluorescence image by, for example, superimposition processing in the embodiments described above, it may also be superimposed on a white-light image.

REFERENCE SIGNS LIST 1, 2, 3, 4 fluoroscopy system
10 endoscope
17 light source device (illumination light source)
20 control unit
29 white-light-image generating section
30 fluorescence-image generating section
31 intensity-distribution generating section
32 peak-detecting section 33 peak-count comparing section (peak-count calculating section)
34 region-extracting section
35 image-combining section
36 button-generating section
37 mode-switching section
38 selected-biopsy-position memory
39 pointer-generating section
43 monitor (image-displaying section)
46 input section (position-designating section, area-designating section)
100 endoscope system
A subject
B, B1, B2 region

The invention claimed is:

1. A fluoroscopy system comprising:
   an illumination light source that emits white light and excitation light for irradiation of a subject;
   a white-light-image generating section that generates a white-light image by capturing the reflected light reflected on the subject irradiated with the white light emitted from the illumination light source;
   a fluorescence-image generating section that generates a fluorescence image by capturing fluorescence emitted from the subject irradiated with the excitation light emitted from the illumination light source;
   an intensity-distribution generating section that generates a fluorescence intensity distribution of pixels of the fluorescence image generated by the fluorescence-image generating section;
   a peak-detecting section that detects a fluorescence-intensity peak in the fluorescence intensity distribution generated by the intensity-distribution generating section;
   a peak-count calculating section that calculates a count of the peak detected by the peak-detecting section;
   an image-combining section that generates a combined image by superimposing a display representing a region including a pixel having the fluorescence intensity at the peak detected by the peak-detecting section on the white-light image or the fluorescence image based on the peak count calculated by the peak-count calculating section; and
   an image-displaying section that displays the combined image generated by the image-combining section.

2. The fluoroscopy system according to claim 1, further comprising a position-designating section via which a desired position is designated in the combined image displayed by the image-displaying section,
   wherein the image-combining section generates a combined image by superimposing a display identifying the position designated by the position-designating section on the white-light image.

3. The fluoroscopy system according to claim 1, wherein the image-combining section generates a combined image by superimposing a display locating the pixel having the fluorescence intensity at the peak on the white-light image.

4. The fluoroscopy system according to claim 1, wherein if the peak-detecting section detects a plurality of peaks, the image-combining section generates a combined image by superimposing a display representing the region on the fluorescence image.

5. The fluoroscopy system according to claim 1, wherein the image-combining section generates a combined image representing a plurality of the regions corresponding to a plurality of peaks at different fluorescence intensities in different manners for each region.

6. The fluoroscopy system according to claim 5, wherein the image-combining section represents the plurality of regions corresponding to the plurality of peaks at different fluorescence intensities in different colors.

7. The fluoroscopy system according to one of claim 1, wherein the image-combining section represents the region by using a boundary line surrounding the region.

8. The fluoroscopy system according to claim 1, further comprising an area-designating section via which a desired area is designated in the combined image displayed by the image-displaying section,
   wherein the image-combining section generates a combined image by further combining an enlarged image of an area of the white-light image corresponding to the area designated by the area-designating section.

* * * * *

UNITED STATES PATENT AND TRADEMARK OFFICE
CERTIFICATE OF CORRECTION

PATENT NO. : 8,440,984 B2
APPLICATION NO. : 13/597978
DATED : May 14, 2013
INVENTOR(S) : Hiromi Shida Page 1 of 1

It is certified that error appears in the above-identified patent and that said Letters Patent is hereby corrected as shown below:

Title Page, item (30) should read as follows:

(30)   Foreign Application Priority Data

March 3, 2010    (JP) .............................. 2010-046568

Signed and Sealed this
Twenty-second Day of October, 2013

Teresa Stanek Rea
*Deputy Director of the United States Patent and Trademark Office*